US010537290B2

(12) United States Patent
De Waele et al.

(10) Patent No.: US 10,537,290 B2
(45) Date of Patent: Jan. 21, 2020

(54) USAGE OF OBSERVED ALARM SETTINGS FOR ALARM MANAGEMENT

(71) Applicant: KONINKLIJKE PHILIPS N.V., Eindhoven (NL)

(72) Inventors: Stijn De Waele, Millwood, NY (US); Larry Nielsen, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 447 days.

(21) Appl. No.: 14/813,213

(22) Filed: Jul. 30, 2015

(65) Prior Publication Data
US 2016/0051206 A1    Feb. 25, 2016

Related U.S. Application Data

(60) Provisional application No. 62/040,475, filed on Aug. 22, 2014.

(51) Int. Cl.
| | | |
|---|---|---|
| *G08B 21/00* | (2006.01) | |
| *A61B 5/00* | (2006.01) | |
| *G16H 50/50* | (2018.01) | |
| *A61B 5/0205* | (2006.01) | |
| *G16H 40/63* | (2018.01) | |
| *G16H 50/30* | (2018.01) | |
| *A61B 5/021* | (2006.01) | |
| *A61B 5/024* | (2006.01) | |
| *A61B 5/08* | (2006.01) | |

(52) U.S. Cl.
CPC .......... *A61B 5/746* (2013.01); *A61B 5/02055* (2013.01); *G16H 50/50* (2018.01); *A61B 5/021* (2013.01); *A61B 5/024* (2013.01); *A61B 5/0816* (2013.01); *G16H 40/63* (2018.01); *G16H 50/30* (2018.01)

(58) Field of Classification Search
CPC ... A61B 5/746; A61B 5/0205; A61B 5/02055; A61B 5/14551; A61B 5/0022; A61B 2560/0242; A61B 5/021; A61B 5/024; A61B 5/0816; G06F 19/3437; G06F 19/3418; G06F 19/3431; G06F 19/3406; G16H 50/50; G16H 40/63; G16H 50/30
USPC .......... 340/540, 573.1, 286.01, 3.1; 600/300, 600/595
See application file for complete search history.

(56) References Cited

U.S. PATENT DOCUMENTS

| | | | | |
|---|---|---|---|---|
| 5,331,549 | A * | 7/1994 | Crawford, Jr. ...... | G06F 19/3406 600/513 |
| 9,554,706 | B2 | 1/2017 | Soomro | |
| 2002/0013518 | A1* | 1/2002 | West ..................... | A61B 5/1113 600/300 |
| 2008/0281168 | A1* | 11/2008 | Gibson ................ | A61B 5/0205 600/301 |
| 2011/0224565 | A1* | 9/2011 | Ong ..................... | A61B 5/4824 600/509 |

(Continued)

FOREIGN PATENT DOCUMENTS

| | | |
|---|---|---|
| WO | 20100095064 A1 | 8/2010 |
| WO | 2014036173 A1 | 3/2014 |

*Primary Examiner* — Anh V La

(57) ABSTRACT

A system to generate medical monitor alarm settings (10) which includes a normative analyzer (36) and/or observational analyzer (48) configured to receive (130) data from logs (32, 34) of a plurality of medical monitors (12), and generate (134, 138) one or more suggested alarm settings (26) based on a constructed model of the received log data.

20 Claims, 4 Drawing Sheets

(56) References Cited

U.S. PATENT DOCUMENTS

2013/0045685 A1     2/2013   Kiani
2013/0278414 A1   10/2013   Sprigg et al.
2015/0018648 A1*   1/2015   Boyer ............... A61M 16/1005
                                                                                                600/323

* cited by examiner

USAGE OF OBSERVED ALARM SETTINGS FOR ALARM MANAGEMENT

FIELD

The following relates generally to medical monitoring. It finds particular application in conjunction with determining alarm settings of medical monitoring devices, and will be described with particular reference thereto. However, it will be understood that it also finds application in other usage scenarios and is not necessarily limited to the aforementioned application.

BACKGROUND

The United States Joint Commission has set National Patient Safety Goals for 2014-2016 that requires healthcare organizations to address alarm fatigue by "establishing policies and procedures for managing alarms" by "checking individual alarm signals for accurate settings." Alarm monitors receive vital signs from patients and send alerts if one or more vital signs exceed one or more minimum or maximum threshold limit values. For example, if a patient's respiration rate rises to a predetermined threshold value or alternatively falls to a predetermined threshold value, an audible or visual message is sent to one or more healthcare practitioners. Monitors are typically delivered with default settings based on literature of the general population, e.g. a normal adult respiration rate is 12-20 breaths per minute. But, populations with different medical conditions may have a different nominal respiration rate. Healthcare organizations are encouraged to review the default settings according to the patient population served and customize the settings according to each healthcare organization policies.

Healthcare organizations typically rely on the default settings, which generate alarms contributing to alarm fatigue. Many healthcare organizations are without mechanisms to identify and manage alarm settings which are appropriate to the patient populations served. Healthcare organizations have relied upon individual healthcare practitioners to identify and change alarm settings for individual patients. Healthcare practitioners are unfortunately not in a position to address customized alarm settings for each patient. Healthcare practitioners may pause or cancel nuisance alarms, and may sometimes change individual settings for a patient based on a history or known condition for the patient. Changing individual alarm settings for a patient calls for a clear understanding of each alarm setting associated with a vital sign, and an evaluation of potential changes in relation to the possible outcomes for the patient, which may be a daunting proposition for the healthcare practitioner managing a group of patients in a dynamic environment. Hence, a gap exists between the default settings and the settings appropriate for each individual patient, which will reduce the overall alarm fatigue. In other words, for situations of a patient having alarms, there are typically no alternatives to the default alarm limit settings that are readily available to a healthcare practitioner or a method to identify alternative alarm settings.

SUMMARY

The following discloses a new and improved usage of observed alarm settings for alarm management which addresses the above referenced issues, and others.

In accordance with one aspect, a system to generate medical monitor alarm settings includes a normative analyzer configured to receive data from logs of a plurality of medical monitors, and to generate one or more suggested alarm settings based on a constructed model of the received log data.

In accordance with another aspect, a method of generating medical monitor alarm settings includes receiving data from logs of a plurality of medical monitors. One or more suggested alarm settings are generated based on a constructed model of the received log data.

In accordance with another aspect, a system to monitor patient vital signs includes a medical monitor and an observational analyzer. The medical monitor is configured to receive monitored vital signs for at least one patient and includes a plurality of sets of alarm settings defined according to a constructed normative model of data from selected medical monitors. Each set of alarm setting includes at least one of an upper and a lower limit for at least one monitored vital sign. The observational analyzer is configured to receive the at least one monitored vital sign in an alarm condition according to a first set of alarm settings and return a recommended second set of alarm settings which places the at least one monitored vital sign in a non-alarm condition.

One advantage is alarm settings are suggested for a healthcare organization based on normative use.

Another advantage resides in alarm settings suggested based on observed changes in vital signs and responses for an individual patient or group of patients by healthcare practitioners.

Another advantage resides in suggested profiles for which healthcare organizations can review and implement as policy changes.

Another advantage resides in options for revising alarm settings for individual patients.

Still further advantages will be appreciated to those of ordinary skill in the art upon reading and understanding the following detailed description.

BRIEF DESCRIPTION OF THE DRAWINGS

The invention may take form in various components and arrangements of components, and in various steps and arrangement of steps. The drawings are only for purposes of illustrating the preferred embodiments and are not to be construed as limiting the invention.

DETAILED DESCRIPTION

Figure 1:
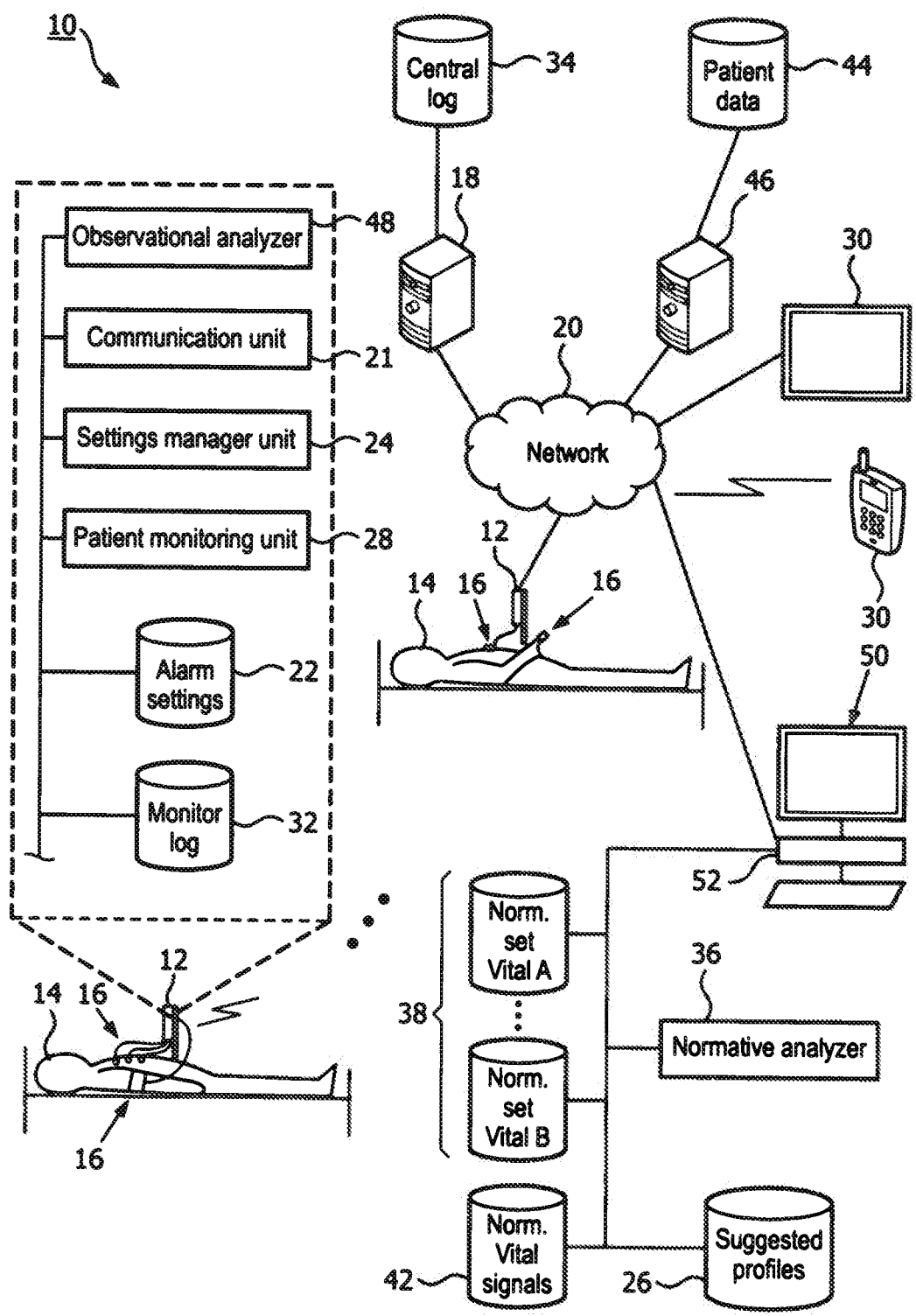
FIG. 1 diagrammatically illustrates an embodiment of a system for usage of observed alarm settings for alarm management with a partial exploded view of a medical monitor.

With reference to FIG. 1, an embodiment of a system 10 for usage of observed alarm settings for alarm management is diagrammatically illustrated. The system 10 includes one or more medical monitors 12, which receive vital sign signal values from monitored patients 14. The vital sign signals are sensed by one or more vital sign monitoring devices 16, such as a non-invasive or invasive blood pressure (BP) monitor, $SpO_2$ or blood oximetry device, respiratory rate (RR) monitor, electrocardiogram (ECG) monitor, Heart Rate (HR) monitor and the like affixed, attached, or otherwise connected to each monitored patient shown with a partial exploded view. The vital sign monitoring devices 16 sense the corresponding vital sign signal and transmit the vital sign signal to the medical monitor 12 as the vital sign signal, e.g. as a waveform and/or as a value. In one embodiment, the system 10 includes a central monitor 18 via a network 20, which receives vital signs from a communication unit 21 of each medical monitor 12, representing a group of centrally monitored patients. The network 20 can include public and/or private networks, wired or wireless networks, cellular and/or data networks, hard-wired or virtual (Cloud-based systems) and combinations. Patients can be ambulatory or non-ambulatory, centralized or distributed geographically, clinic based, home based or hospital based, intensive care unit (ICU) based, and the like.

Each medical monitor 12 includes alarm settings or alarm profiles 22 managed by a settings manager processor, unit, device, or means 24. The alarm settings 22 define alarm threshold values for one or more vital signs, e.g. RR, ECG, $SpO_2$, HR, etc. Alarm settings can include one or more upper and/or lower limit values for a vital sign signal. For example, a set of settings or a profile includes a lower limit of 50 and an upper limit of 120 for the heart rate (HR) vital sign. Settings for a one vital sign can include multiple upper and/or lower limits, e.g. two upper limits and one lower limit, two upper limits and two lower limits, one upper limit, two lower limits, etc., such as indicative of High Priority ("yellow") or Critical ("red") care response situations. The alarm settings 22 can be representative of a particular patient population, segmented by disease, condition, age, etc. For example, one set of settings can represent vital sign limits for adult cardiac patients, another set of settings for neonatal patients, yet another settings for pre-admitted patients, and the like. The alarm settings 22 can include further refinement based on monitored vital signs. For example, four sets of settings or profiles can be defined for cardiac patients, which represent different normative populations based on correlated monitored vital sign signals and/or alarm limits. Data elements in the alarm settings 22 for each vital sign include an identification of the vital sign, e.g. RR, HR, etc., one or more upper alarm limits and/or one or more lower limits. The data elements can include a label, a delay, a severity, and/or a validity indicator. The validity indicator selectively turns off the alarm while continuing to monitor and report the vital sign.

The settings manager 24 is configured to receive changes to the alarm settings 22 by entry of a healthcare practitioner and/or electronic transmission from a suggested profile 26 data store. For example, default settings according to a suggested profile can be loaded into the medical monitor and then revised by the healthcare practitioner. In another example, the healthcare practitioner loads the settings into the medical monitor by data entry.

A medical monitoring processor, unit, device, or means 28 receives the vital sign signal from each of the vital sign monitoring devices 16. The medical monitoring unit 28 compares each vital sign signal to the patient alarm settings 22, and sends alerts based on the comparison to one or more alerting devices 30, such as a local audio and/or video device operatively connected to the medical monitor, a display device mounted in a hospital unit, a healthcare practitioner desktop or mobile computing device, and the like. The medical monitoring unit 28 stores received monitoring data and/or setting data in a monitor log 32. The monitor log 32 can include a vital sign signal history, an alarm setting change history, alarm settings at an alarm event, and/or vital sign signals according to alarm events or other time intervals. In one embodiment, a central log 34 receives the monitoring data and/or setting data from the medical monitors 12 for groups of patients centrally monitored. In another embodiment, the monitoring data and/setting data can be distributed between or duplicated between the individual medical monitors 12 and the central monitor.

A normative analyzer or means 36 receives the monitoring data and/or setting data from individual monitor logs 32 and/or central logs 34. The individual monitor logs 32 and central logs 34 may be selected as a normative population. For example, logs from organizations, organizational units, and/or individual patients for which alarm settings are considered desired norms or best practices are selected. The normative analyzer 36 extracts values from the selected logs representative of normative vital sign alarm settings 38 and/or normative vital sign signals 42, constructs a model of the extracted data, and generates the suggested alarm settings 26 based on the constructed normative model.

The normative analyzer 36 can further receive medical information or patient data 44 from other patient care systems 46, such as patient medical records, laboratory medicine information systems, radiology information systems, and the like. The normative analyzer 36 uses the medical information, such as patient condition, patient diagnosis, and the like to further refine the constructed model and/or the suggested profiles 26. For example, patients with a diagnosis of stroke are analyzed as a group and suggested settings are generated for the stroke patients, while patients with a diagnosis of heart arrhythmia or heart attack are analyzed as a separate group and a different suggested set of settings is generated for the heart attack patients. Multiple sets of settings or profiles can be generated from each patient population. For example, multiple profiles can be generated from stroke patients. One profile defines one set of alarm settings.

The settings manager 24 updates the alarm settings 22 based on the suggested profiles 26. The settings manager unit 24 can be configured to receive input from a responsible healthcare practitioner validating each suggested profile for use. The validation can include site instructions which define the scope and conditions for use, such as patient populations to which the profile applies and exclusions. For example, a suggested profile for admitted emergency room patients is incorporated into the alarm settings with exclusions for children, infants, head injuries, and the like. In another example, three of four suggested profiles or groups of alarm settings for an intensive care unit (ICU) are incorporated into the alarm settings for an ICU medical monitor and the fourth is rejected by the responsible healthcare practitioner.

An observational analyzer or means 48 generates one or more suggested setting changes and/or further refines based on an observational analysis of the vital sign signals and/or patient data. In one embodiment, a healthcare practitioner selects a patient or patient population for recommended changed alarm settings and the observational analyzer 48 recommends one or more alarm setting changes. For example, a healthcare practitioner communicatively connects to a medical monitor 12 using an alerting device 30 and/or other computing device 50, and selects the patient and/or vital sign for review, and the observational analyzer generates a setting change in response. In another embodiment, the observational analyzer 48 recommends changes to alarm settings for the patient based on current vital sign signals and/or patient data 44, and sends the recommended changes to the alerting device 30 or other computing device 50. Over time, based on recent medical history, vital sign signals and/or alarm data, the patient can be reassigned or recommended to be reassigned to a different alarm profile or changed settings. The recommended changes or profiles can include an individual alarm setting or a group of settings. The recommended changes or profiles can include settings for one vital sign monitored or multiple vital signs monitored. For example, one patient is admitted to an Emergency Department and monitored with a set of alarm settings A. As the patient condition is reviewed, vital sign signals monitored and conditions identified, the observational manager 48, recommends a change to a set of settings B, such as representative of a head injury or heart medication history, which may include increases and/or decreases in one or more vital sign settings. The observational manager 48 may be located with the medical monitor 12 or within the computing device 50.

The various managers, units, or analyzers 21, 24, 28, 36 and 48 are suitably embodied by a data processing device, such as an electronic processor or electronic processing device 52 of the computing device 50, or by a network-based server operatively connected with the computing device 50 by the network 20, or so forth. Moreover, the disclosed normative analysis and observational analysis techniques are suitably implemented using a non-transitory storage medium storing instructions (e.g., software) readable by a data processing device and executable by the data processing device to perform the disclosed normative analysis and observational analysis techniques. Suitable storage media include optical, magnetic, or solid state memory such as CD, DVD, hard disks, diskette, RAM, flash, etc.

The alarm settings or alarm profiles 22, the suggested profiles 26, the monitor log 32, the central log 34, the normative settings 38, the normative vital sign signals 42, and the patient data 44 are suitably embodied by a data store, such as a configured storage medium. The configured storage medium can include file structures, object or relational databases, data structures, non-transitory computer readable media, and the like.

Figure 2:
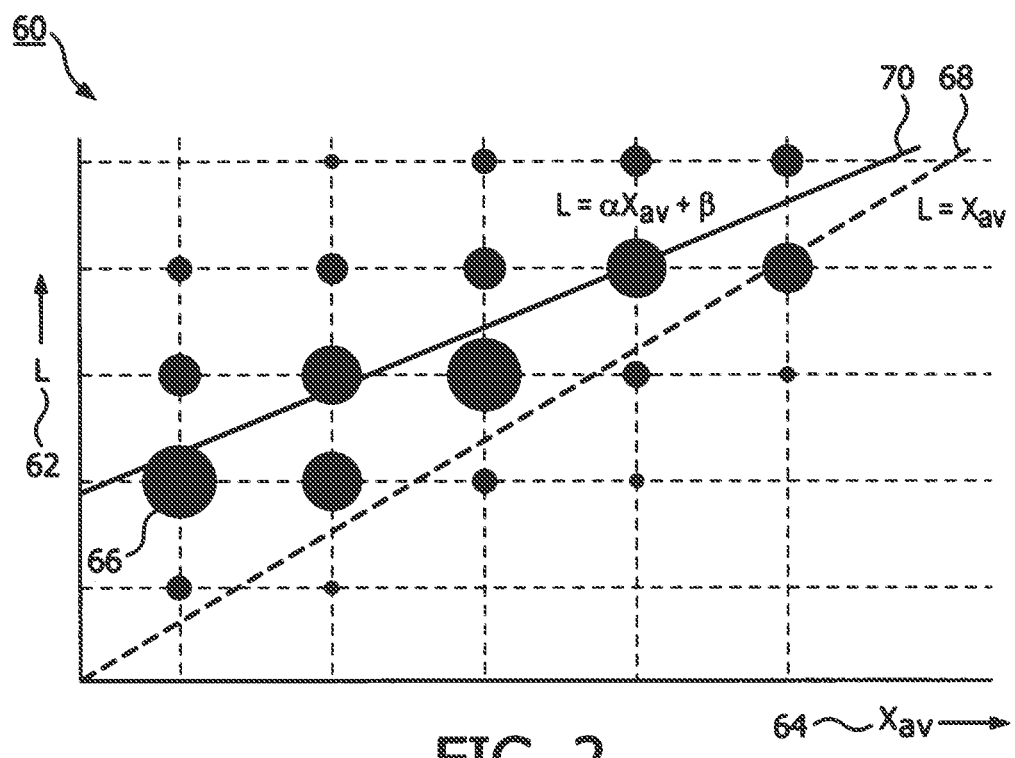
FIG. 2 illustrates an exemplary correlation plot and regression analysis of one alarm limit versus average vital sign values.

With reference to FIG. 2 an exemplary correlation plot 60 and regression analysis of one alarm limit and average vital sign values is illustrated. The data values are from a population or collection of medical monitor data. The correlation plot 60 includes alarm settings 38 represented as discrete values of alarm settings or limits (L) 62 at a time t on the vertical axis and corresponding vital sign signals 42 represented as values of average vital sign signals ($X_{av}$) 64 at the time t on the horizontal axis. For example, the correlation plot can represent a high limit (L) for respiratory rate (RR) versus average respiratory rate ($X_{av}$). In the figure, values of L and $X_{av}$ are combined into discrete intervals from continuous values, e.g. a single value representing a range of values, such as a center value. The size of each dot 66 plotted represents a frequency of usage or a frequency of occurrence in population of data, e.g. medical monitor 12 logs 32, 34. A line 68 representing L=$X_{av}$ is shown for reference. As an alternative to the representation in the figure, continuous vital signs values ($X_{av}$) can be used, as well as continuous limit values (L).

A regression analysis fits a second line 70 to generate a function L=$\alpha X_{av}$+$\beta$ where $\alpha$ and $\beta$ are derived from the regression. The generated function summarizes the correlation between the vital sign signal values and the alarm limits. The regression analysis can include functions of $X_{av}$, such as $X_{av}^n$, $\ln(X_{av})$, etc. The generated function or a table created from the generated function provides suggested alarm setting values based on observed vital sign signal values. For example, monitoring of a patient's HR for a predetermined period is used to generate a suggested alarm setting value using the function L=$\alpha X_{av}$+$\beta$ with values from the regression. The regression analysis can be generalized to a multi-parameter correlation of multiple alarm setting or limit values and corresponding multiple vital sign signal values, e.g. L=($L_1, L_2, \ldots, L_n$) and X=($X_1, X_2, \ldots, X_n$). For example, alarm limits and signal values of respiratory rate (RR) and $SpO_2$ are correlated including cross-correlations, e.g. RR and/or $SpO_2$ signal values are included in the generated functions of RR and/or $SpO_2$ alarm settings.

The normative analyzer recommends new or suggested alarm settings 26 based on analysis of normative populations. The recommended settings are based on normative or best practice use of alarm settings and/or monitored vital sign signals. The observational analyzer 48 recommends new alarm settings, which are adaptive to the individual patient. The recommended alarm settings can be constrained or subject to sets of the settings, e.g. change from a first set of alarm settings X to second set of alarm settings Y subject to healthcare practitioner approval. The recommended alarm setting changes can include changes in a single alarm setting value, or changes in combinations of one or more alarm setting values of one or more vital signs. For example, a change in upper limit value of RR is recommended, changes in upper and lower limit values of RR are recommended, or changes in upper and lower limit values of RR and $SpO_2$ are recommended, etc. Also, the recommended changes may include other alarm settings besides limits, e.g. an alarm delay or inhibition time; switching an alarm on or off; or changing the alarm severity, e.g. from "High Priority" to "Low Priority".

Figure 3:
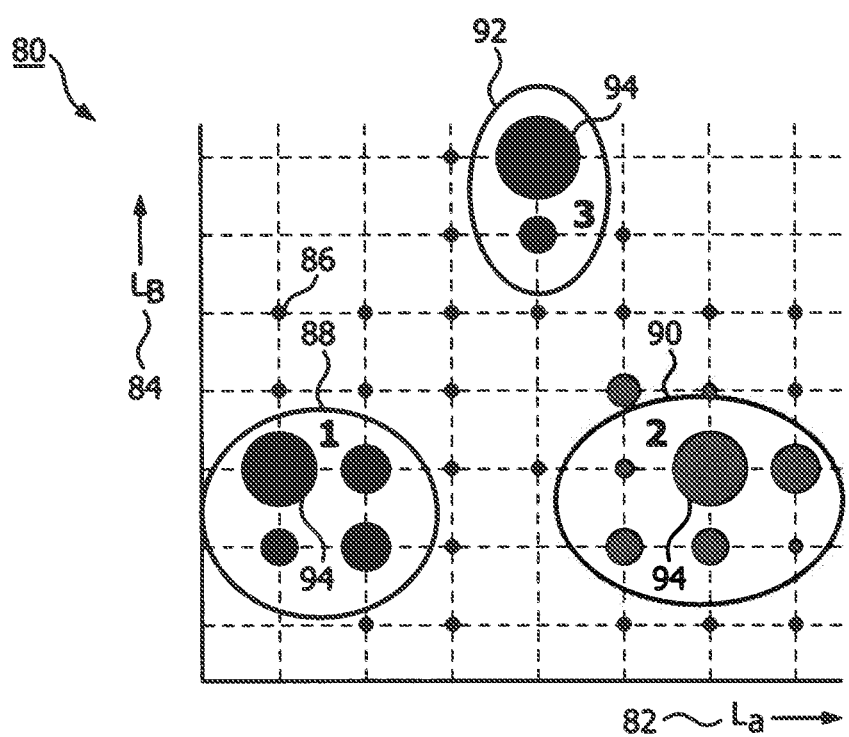
FIG. 3 illustrates an exemplary correlation plot and cluster analysis of two alarm limits.

With reference to FIG. 3, an exemplary correlation plot and cluster analysis of two alarm settings or limits 80 is illustrated. Normative values of a first alarm limit $L_A$ 82 are represented on the horizontal or x-axis and normative values of a second alarm limit $L_B$ 84 are represented on the vertical or y-axis. The limits are represented in the plot as discrete intervals with dots 86 sized to represent the frequency of occurrence in the analyzed monitor log(s) 32, 34 or extracted normative settings 38 and/or normative vital sign signals 42.

From the correlation plot, clusters 90, 92 are identified either manually and/or using automated clustering means, such as a k-means algorithm. A representative or center value 94 of each cluster is computed as an alarm setting value in one or more suggested profiles 26. The suggested alarm settings values represent normative alarm setting values for the selected and analyzed monitor log(s) 32, 34, or analyzed normative settings 38.

Figure 4:
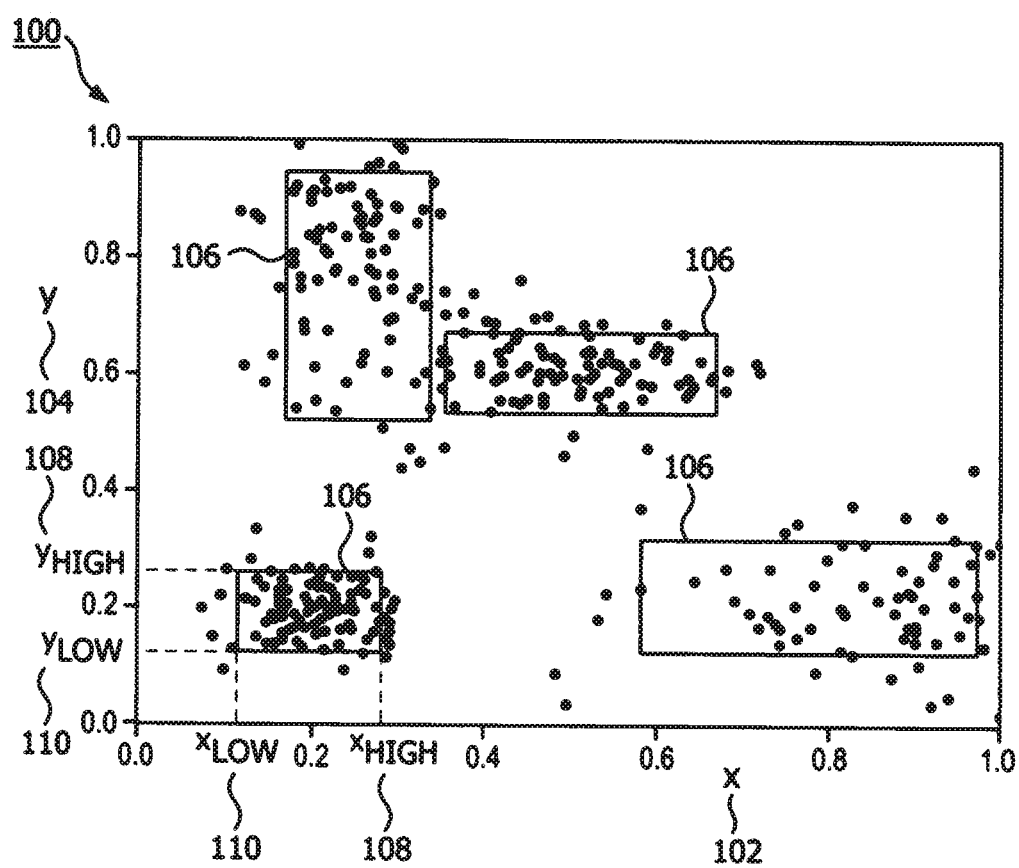
FIG. 4 illustrates an exemplary scatter plot and cluster analysis of two vital sign signals.

With reference to FIG. 4, an exemplary scatter plot and cluster analysis of two normative vital sign signals 100 are illustrated. Values of a first vital sign signal X 102 are represented on the horizontal axis or x-axis scaled to a normalized scale (0,1), and normalized values of a second vital sign signal y 104 are represented on the vertical axis or y-axis scale. The scatter plot represents the correlation between vital sign signal values of two vital signs, such as RR and $SpO_2$, HR and BP, etc. The analysis of the two vital sign signals extends to a multivariate analysis of n vital signs where n represents the number of different vital signs.

Clusters 106 are identified manually and/or using an automated clustering means or routine, or guided by external data such as patient diagnosis. High limit setting values 108 and low limit setting values 110 are derived from at least one cluster distribution, e.g. taking a 1% and 99% quantiles, ±2 standard deviations, etc. Suggested profiles 26 include one or more sets of the derived high and low values. Other medical information can be used to further identify or refine the clusters. For example, patient condition or diagnosis, hospital unit, or other medical information can correlate with the clusters and/or vital sign signals. One or more suggested profiles 26 are generated from the analysis. The data of two vital sign signals is represented in the normative vital sign signals 42, which is obtained from the monitor logs 32, 34. The cluster identification is part of the normative analysis.

Figure 5:
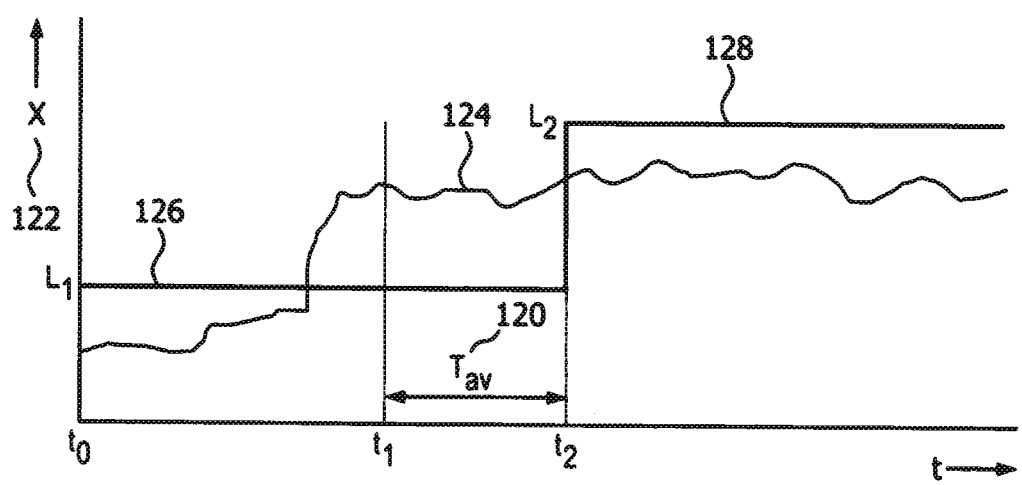
FIG. 5 illustrates an exemplary vital sign signal and vital sign setting change graph.

With reference to FIG. 5, an exemplary vital sign signal values and vital sign alarm setting graph is illustrated. Vital sign signals are represented by an average of the vital sign signal values over a selected time interval $t_1$ to $t_2$, such as 15 minutes or an hour, although it could be longer or shorter. The average of the vital sign values over the selected time interval $T_{av}$ 120 is represented by a variable $X_{av}$. The values of the vital sign signals in FIGS. 2 and 4 can be represented by $X_{av}$. In one embodiment, $X_{av}$ represents a variable which includes a time interval preceding a change in an alarm setting. Time is represented on the horizontal axis. The values of a vital sign signal X 122 are represented on the vertical axis. The graph plots the vital sign signal 124 over time. A first upper limit value $L_1$ 126 is represented as a line from a time $t_0$ to $t_2$, and a second upper limit value $L_2$ 128 beginning at $t_2$. The second upper limit represents a changed alarm setting value. The values of the vital sign signal 124 are initially lower than the threshold limit value $L_1$ at time $t_0$ and greater than the threshold limit value $L_1$ at time $t_1$ indicative of the alarm condition. In one embodiment, after the vital sign has exceeded $L_1$ for a time sufficiently long to infer that exceeding $L_1$ is not a short term aberration, the data is collected over $T_{av}$ 120 and a new alarm limit is recommended. When the analysis produces the new recommended alarm limit at time $t_2$, the alarm limit value is changed to a value greater than the vital sign signal value, e.g. $L_2 > X$. With this change, the patient is no longer in the state where the vital sign meets the alarm condition, e.g. non-alarm condition. The observed change from a normative alarm setting value, such as $L_1$, to a different alarm setting value, such as $L_2$, provides a value for observational modeling. The changed setting, an increase or a decrease, related or unrelated to an alarm condition, provide values for observational modeling or deviations from normative values. For example, a weight can be assigned to changes in alarm settings, e.g. the model includes variable of values representative of alarm settings which are changed values from a default, organizational determined, installed setting. In other embodiments, the analysis can include the same or different weights for changed alarm settings related to an alarm condition.

In one embodiment a variable defines the delay in change from a first alarm setting to a second alarm setting, the first alarm setting being in the alarm state, and the second alarm setting being in a non-alarm state. The variable can be used to identify suggested settings values, e.g. new values. The variable can be used to identify a time interval, either a minimum or a maximum after which a different alarm setting value is recommended. For example, an alarm condition is triggered with a first alarm setting, and after a predetermined time interval or function thereof is satisfied, a second alarm setting is recommended. The alarm setting change can include different upper and/or lower limit values. The alarm setting change recommendation can be presented as a pull option, e.g. as requested by a healthcare practitioner e.g. after an alert has occurred, or as a push option, e.g. notice sent with a recommendation to alerting devices 30. In one embodiment, the variable includes alarm counts as a weighting and/or as an additional variable.

When correlating vital sign signals values with alarm setting values, the vital sign signal value in the time interval $[t_1, t_2]$ just before the setting change can be used in creating correlation graphs such as FIG. 2. The time $t_1$ is determined by subtracting a given averaging time from the setting change time $t_2$. Conversely, as a patient's vital signs improve, the alarm setting might be lowered at a later time.

Figure 6:
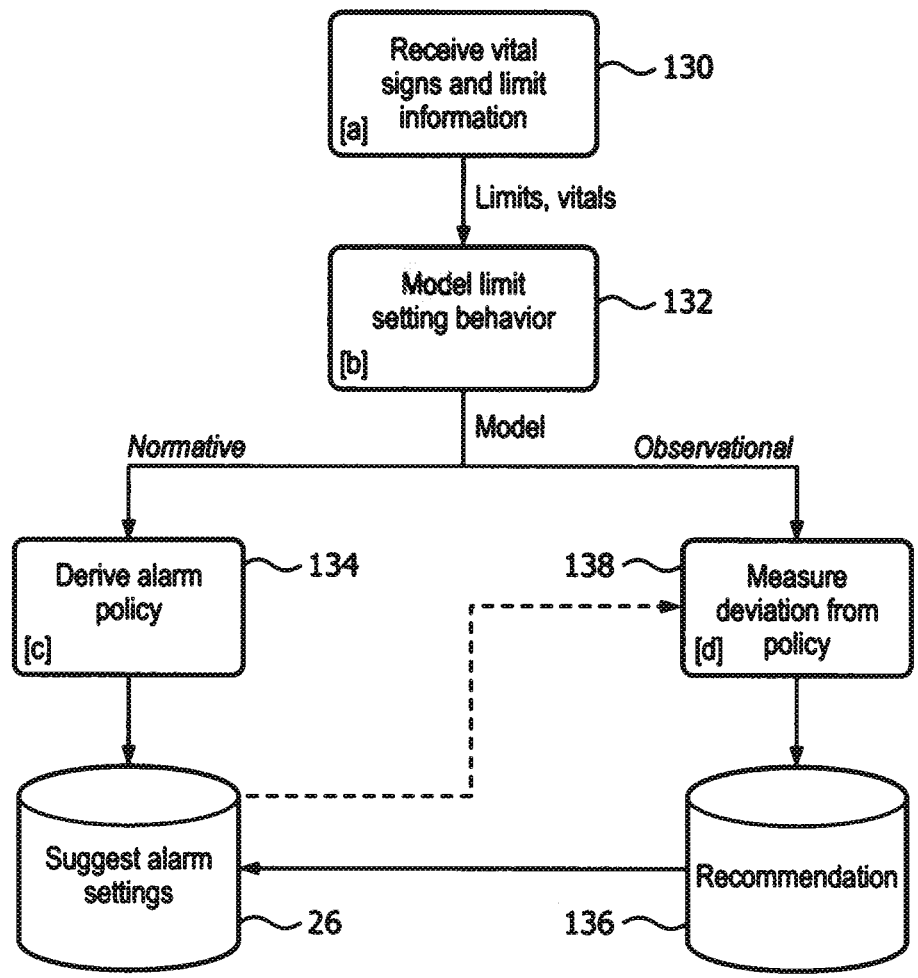
FIG. 6 flowcharts one method of usage of observed alarm settings for alarm management.

With reference to FIG. 6, one method of usage of observed alarm settings for alarm management is flowcharted. In a step or with a module 130 vital sign signals and/or alarm setting data is received. The vital sign signals and/or alarm setting data are received on a computer storage medium, such as magnetic disk, solid state disk, optical disk, and the like. The vital sign signals and/or alarm setting information can be obtained by electronic transfer of monitor logs 26, central logs 34, and/or patient alarm settings 22. The electronic transfer can occur over a network or by direct access and copying of data from individual medical monitors 12 and/or central monitors 18. Selection of data to derive the normative model occurs by selecting individual medical monitors 12, groups of medical monitors, organizational units, and/or organizations which are considered best practices. The step can include receiving other medically related information, e.g. patient diagnosis or condition, treatment, laboratory results, etc.

In a step or with a module 132, an analysis of the normative settings 38 and/or normative vital sign signals 42 creates one or more models. Examples of the analysis are described in reference to FIGS. 2-5. The step can include analysis with correlations, cross-correlations, single or multivariate regression, cluster analysis, and/or single or multivariate analysis of variance performed with a configured computer processor. The step can include conversion of continuous values to discrete intervals. The step can include identification of upper and/or lower alarm settings. The step can include different combinations of vital signs, e.g. alarm limits for one or more vital signs based on one or more of the vital signs as well as other factors, such as time of day, ambient temperature or barometer pressure, etc. The step can include identification of recommended target patient populations, e.g. according patient condition, diagnosis, demographic, etc., such as received in the medically related information.

Suggested alarm settings or profiles 26 are generated in a step or by a module 134 according the created model of the normative medical monitor data. The generated suggested alarm profiles 26 include settings for one or more vital sign alarms. The settings can include one or more upper and/or lower limits for one or more vital signs. The suggested alarm profiles 26 can be segregated by identified target patient population. For example, the profiles can be segregated by organizational care unit, such as cardiology unit, emergency department, hypertension unit, etc. In another example, the profiles can be segregated based on measured vital sign signals, such as an initial or first set of settings and a second set of settings transitioned from the first set of settings based on a patient vital sign signal values after a predetermined period of time. The suggested profiles 26 represent a derived alarm policy of normative settings according to modeled best practices. The suggested profiles 26 can be installed by an organization, organizational unit, or healthcare practitioner on one or more medical monitors 12 via the settings manager unit 24.

A recommendation 136 for a changed alarm setting 22 is generated in a step or with a module 128 based on an observational analysis. The observational analysis, such as described in reference to FIG. 5, includes changes in alarm settings 22 of medical monitors 12 modeled as deviations from policy. The recommendation 136, which includes one or more changed or different settings, is generated from the modeled changes. For example, a modeled observational analysis identifies a set of settings, A, for $SpO_2$ and HR, which deviates from general use in organizational units of type R. In another example, a modeled observational analysis identifies a set of settings, B, for BP of a target patient population with a condition X, which deviates from general use in an organization. The recommendation 136 can be separately provided or incorporated into one or more suggested profiles 26. Also, observed deviations from the policy can lead to initiation of additional training in alarm management for the clinical staff.

In one embodiment, the recommendation 136 in response to received vital sign signals and/or an alarm condition.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A system to generate medical monitor alarm settings, comprising:
    a plurality of medical monitors;
    a normative analyzer configured to:
        receive data from logs of the plurality of medical monitors, the received data including at least alarm settings for a plurality of monitored vital signs and alarm conditions including time averaged vital sign signal values, alarm settings for the plurality of monitored vital signs, and changed alarm settings for the plurality of monitored vital signs; and
        generate one or more suggested alarm settings based on a constructed model of the received log data.

2. The system to generate medical monitor alarm settings according to claim 1, wherein the received data from the logs further includes at least one of:
    vital sign signal values for a plurality of monitored vital signs; and
    vital sign signal values with corresponding changes to alarm settings for the plurality of monitored vital signs.

3. The system to generate medical monitor alarm settings according to claim 1, wherein the generated suggested alarm settings includes settings according to a defined target patient population.

4. The system to generate medical monitor alarm settings according to claim 1, further including:
    an observational analyzer configured to recommend the one or more suggested alarm settings for a medical monitor in an alarm condition to one of the generated suggested alarm settings.

5. The system to generate medical monitor alarm settings according to claim 4, wherein the observational analyzer is configured to:
    send the recommended change to at least one alerting device receiving the alarm condition; and
    receive acceptance of the recommended change and change the alarm settings in the medical monitor for the patient to the accepted alarm settings.

6. The system to generate medical monitor alarm settings according to claim 1, wherein the received data from the logs is selected to include at least one of normative settings and normative vital sign signals to construct the model.

7. The system to generate medical monitor alarm settings according to claim 1, wherein the normative analyzer is configured to construct the model using at least one of:
    a regression analysis of the settings and vital sign signals;
    a cross-correlation of the settings for a plurality of vital signs; or
    an analysis of variance of the settings and vital sign signals.

8. The system to generate medical monitor alarm settings according to claim 1, wherein the normative analyzer is configured to identify clusters in at least one of the normative settings and the normative vital sign signals.

9. The system to generate medical monitor alarm settings according to claim 1, wherein the normative analyzer weights the changes in settings with a count the number of repeating alarm conditions and a variable representing the weighted changes in settings in the constructed model.

10. The system to generate medical monitor alarm settings according to claim 1, wherein the constructed model is based on at least changed alarm settings for at least one monitored vital sign.

11. The system to generate medical monitor alarm settings according to claim 1, further including:
    a profile manager configured to control the medical monitors to change the alarm settings to the suggested alarm settings.

12. A non-transitory computer-readable storage medium carrying software which controls one or more data processing devices to perform a method of generating medical monitor alarm settings, the method comprising:
- receiving log data from logs of a plurality of medical monitors, the received log data including at least changed alarm settings for a plurality of monitored vital signs;
- constructing a model of the received log data by at least a regression analysis of the changed alarm settings and vital sign signals; and
- generating one or more suggested alarm settings based on the constructed model of the received log data.

13. The non-transitory computer-readable storage medium according to claim 12, wherein the received log data further includes at least one of:
- vital sign signal values for the plurality of monitored vital signs;
- vital sign signal values with corresponding changes to alarm settings for the plurality of monitored vital signs; and
- alarm conditions including time averaged vital sign signal values and alarm settings for the plurality of monitored vital signs.

14. The non-transitory computer-readable storage medium of generating medical monitor alarm settings according to claim 12, wherein the generated suggested alarm settings includes settings according to a defined target patient population.

15. The non-transitory computer-readable storage medium of generating medical monitor alarm settings according to claim 12, wherein the received data from the logs is selected to include at least one of normative settings and normative vital sign signals to construct the model.

16. The non-transitory computer-readable storage medium of generating medical monitor alarm settings according to claim 12, wherein the model is further constructed by an analysis of variance of the settings and vital sign signals.

17. The non-transitory computer-readable storage medium of generating medical monitor alarm settings according to claim 16, wherein constructing includes identifying clusters at least one of the normative settings, the normative vital sign signals, and changed alarm settings.

18. The non-transitory computer-readable storage medium of generating medical monitor alarm settings according to claim 12, wherein the constructed model is further based on at least one of:
- a correlation of new alarm settings with averaged vital sign signal values at times the new alarm settings occurred; and
- at least one time average vital sign signal values.

19. A system to monitor patient vital signs, comprising:
- a medical monitor configured to receive monitored vital signs for at least one patient, vital sign signal values for a plurality of monitored vital signs, changed alarm settings for the plurality of monitored vital signs, vital sign signal values with corresponding changes to alarm settings for the plurality of monitored vital signs, and alarm conditions including time averaged vital sign signal values and alarm settings for the plurality of monitored vital signs, and includes a plurality of sets of alarm settings defined according to a constructed normative model of data from selected medical monitors, the model being constructed by a regression analysis of the settings and vital sign signals, a correlation of at least one of the settings, the vital sign signals, and changed alarm settings, a cross-correlation of the settings for a plurality of vital signs, and an analysis of variance of the settings and vital sign signals, each set of alarm setting includes at least one of an upper and a lower limit for a plurality of monitored vital signs; and
- an observational analyzer configured to receive the plurality of monitored vital signs in an alarm condition according to a first set of alarm settings and return a recommended second set of alarm settings which places the plurality of monitored vital signs in a non-alarm condition.

20. The system to monitor patient vital signs according to claim 19, further including:
- a profile manager configured to control the medical monitors to change alarm settings to the suggested alarm settings.

* * * * *